United States Patent [19]

Watanabe et al.

[11] 4,304,670

[45] Dec. 8, 1981

[54] BLOOD FILTER WITH AIR TRAP AND DISTRIBUTING CHAMBER

[75] Inventors: Masaharu Watanabe, Ichikawa; Masaru Wada, Wako, both of Japan

[73] Assignee: Terumo Corporation, Tokyo, Japan

[21] Appl. No.: 134,427

[22] Filed: Mar. 27, 1980

[30] Foreign Application Priority Data

Apr. 3, 1979 [JP] Japan .................................. 54-39941
Apr. 20, 1979 [JP] Japan .................................. 54-48705

[51] Int. Cl.³ ............................................ B01D 35/02
[52] U.S. Cl. .................................... 210/446; 210/456
[58] Field of Search ............... 210/446, 461, 456, 486, 210/346, 343, DIG. 23

[56] References Cited

U.S. PATENT DOCUMENTS 3,730,353 5/1973 Krasen et al. ................... 210/461 X
4,170,056 10/1979 Meyst et al. ..................... 210/446 X

FOREIGN PATENT DOCUMENTS 52-116969 9/1977 Japan .................................. 210/446

Primary Examiner—Frank A. Spear, Jr.

Attorney, Agent, or Firm—Frishauf, Holtz, Goodman and Woodward

[57] ABSTRACT

A blood filter device has a housing including a frame, which is provided at opposite ends with an inlet and an outlet and extends in a plane containing a line connecting the inlet and outlet, and a pair of side plates extending on opposite sides of the frame and defining a filtering space together with the frame. The housing accommodates a filter support and a pair of flat filter elements disposed on opposite sides of the filter support such that each filter element defines together with the filter support a blood-exit space communicating with the outlet and also defines together with the associated side plate a blood-entering space communicating with the inlet. Between the filter support and inlet is provided a distributing and air trapping chamber communicating with the individual blood-entering spaces and defining a space to receive blood from the inlet to trap air contained in the blood and present in the filter device to prevent the air from reaching the filter elements. A distributing piece, which serves to distribute blood introduced through the inlet into the distributing chamber to the individual filtering blood spaces, extends from the filter support into the distributing chamber.

8 Claims, 4 Drawing Figures

BLOOD FILTER WITH AIR TRAP AND DISTRIBUTING CHAMBER

BACKGROUND OF THE INVENTION (1) Field of the Invention

This invention relates to a filter device and, more particularly, to a filter device which is suitable for removing microaggregates from blood.

(2) Description of the Prior Art

Blood for transfusion purposes contains microaggregates which are produced during the storage of the blood. If the blood is transfused to a patient without removing the microaggregates will, they cause various adverse reactions. Also, in dialyzing blood similar problems will arise if microaggregates which have been attached to the filtering surfaces of a dialyzer are released therefrom and mixed with blood remaining in a dialysis circuit at the time when the blood is returned into the patient's body by blowing air from the inlet side of the dialyzer after the dialysis is completed.

There have been developed various blood filter devices for removing microaggregates from blood. These filter devices include those of a soft bag type capable of deformation according to the rate of flow of blood and those of a rigid type incapable of deformation. These two kinds of filters have their respective merits and demerits so that in practice they are used alternatively according to the desired end use.

Japanese Patent Application Disclosure No. 52-116969 (laid open to the public on Sept. 30, 1977 in Japan) discloses a rigid blood filter device, in which a blood inlet and a blood outlet are provided such that they are substantially aligned with each other, and which has a housing extending in a direction at right angles to a line connecting the blood inlet and outlet. A filter element is provided within the housing such that it extends in a direction at right angles to the afore-mentioned line.

Since in this filter device the housing extends in a direction crossing the line connecting the inlet and outlet, it takes much space so that inconveniences exist in its handling in clinical use. In addition, blood is brought into contact with the filter element in a direction at right angles thereto so that it chiefly passes through only a central portion of the element (that is, partial flow results). Thus, there is a deficiency that the entire surface of the filter element cannot be uniformly and effectively used.

Further, a filter element, in general, tends to be clogged if its filtering efficiency is increased under a fixed filtering area, while the filtering efficiency is lowered if mesh size is increased to prevent clogging. Therefore, it is necessary to enlarge the filtering area in order to provide a filter element having a high filtering efficiency. In this connection, if the filter element is simply enlarged in such a filter device as in Japanese Disclosure No. 52-116969, the resultant device would become large in size, presenting an inconvenience in handling.

SUMMARY OF THE INVENTION

An object of the invention, accordingly, is to provide a rigid filter device which permits the entire surface of a filter element to be used uniformly and effectively.

Another object of the invention is to provide a small filter device which occupies less space and permits convenient handling in clinical use, while having a high filtering efficiency and a large filtering area.

According to the invention, there is provided a blood filter device, comprising:

a housing including a frame provided at opposite ends thereof with an inlet and an outlet and extending in a plane containing a line connecting the inlet and outlet, and a pair of side plates secured to opposite sides of the frame and defining a filtering space together with the frame;

a filter support disposed within the housing;

a pair of flat filter elements disposed on opposite sides of the filter support such that each filter element defines together with the filter support a blood-exit space communicating with the outlet and defines together with the associated side plate a blood-entering space communicating with the inlet;

a distributing chamber defined between the filter support and inlet and communicating with each blood-entering space, said distributing chamber having a space sufficient to receive blood from the inlet and to release and trap therein air present in the filter device; and a distributing member extending from the filter support into the distributing chamber and functioning to distribute blood having been introduced through the inlet into the distributing chamber to the blood-entering spaces.

DETAILED DESCRIPTION OF THE PREFERRED EMBODIMENT

Figure 1:
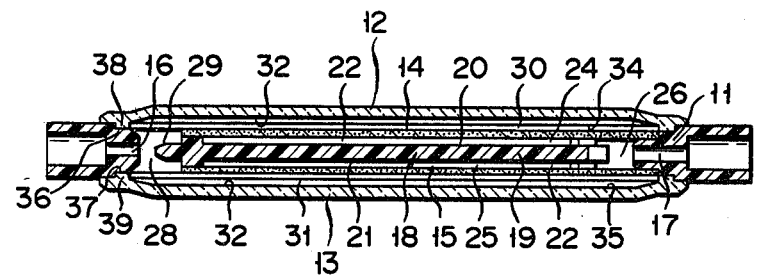
FIG. 1 is a sectional view showing an embodiment of the filter device according to the invention.
Figure 2:
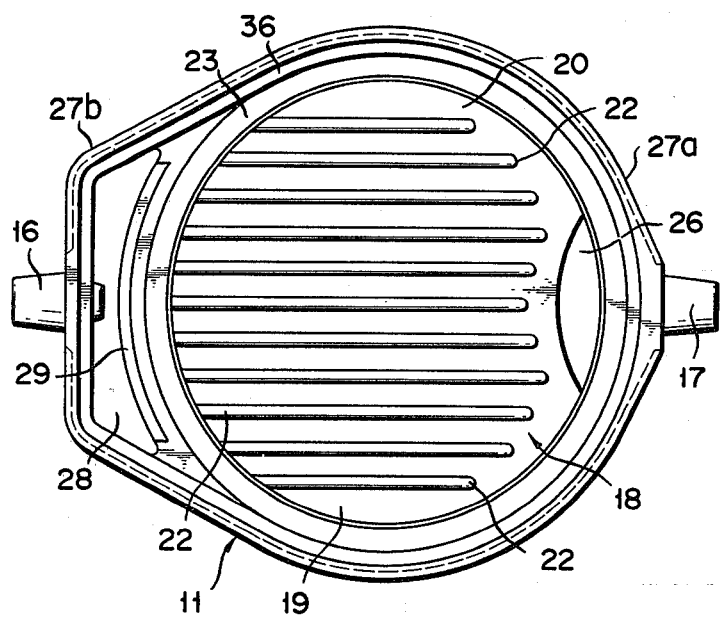
FIG. 2 is a plan view showing a frame and a filter support in the embodiment of FIG. 1.
Figure 3:
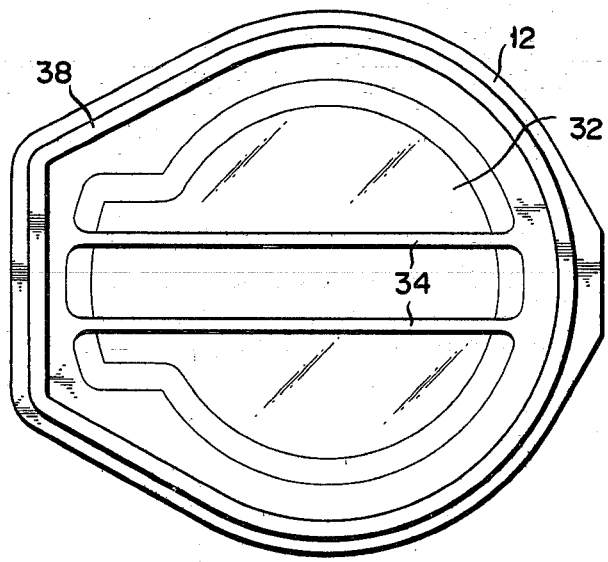
FIG. 3 is a plan view showing a side plate in the embodiment of FIG. 1.

FIGS. 1 to 3 show a first embodiment of the invention. FIG. 1 shows a sectional view of the filter device taken along a line connecting a blood inlet 16 and a blood outlet 17. Referring to FIG. 1, the illustrated filter device comprises a housing, which includes a frame 11 having a relatively low peripheral wall and a pair of side plates 12 and 13 made of a transparent plastic material and respectively provided on the opposite sides of the frame to define together therewith an inner filtering space. The transparency of the side plates 12 and 13 permits observation of the inside thereof. The frame 11 is provided at opposed end positions with a blood inlet 16 and a blood outlet 17, which communicate with the filtering space inside the housing through the wall of the frame 11. Within the filtering space, a filter support 18 for supporting a pair of filter elements 14 and 15 is disposed such that it extends along a line connecting the inlet 16 and outlet 17 and divides the filtering space into two sections.

The filtering elements 14 and 15 are flat in shape and respectively installed on the opposite sides of the filter support 18. The filter element 14 defines together with the side plate 12 a blood-entering space (or upstream space) 30 and also defines together with the filter support 18 a blood-leaving or blood-exit space (or downstream space) 24. Likewise, the filter element 15 defines together with the side plate 13 a blood-entering space 31 and also defines together with the filter support 18 a blood-exit space 25. Where the filter elements 14 and 15 are used for filtering stored blood, they each have a five-layer structure consisting of a mesh screen of a plastic material such as nylon and having a mesh size of 170 to 200μ, a non-woven fabric sheet of a plastic material such as nylon and having a thickness of about 200μ and a mesh size of about 35μ, and three non-woven fabric sheets of a plastic material such as nylon and having a thickness of about 350μ and a mesh size of 25μ, these layers being laminated in the mentioned order, and are installed such that the mesh screen is on the side of the blood-entering space. With this arrangement, relatively large microaggregates are captured by the non-woven fabric sheets, so that the element will not be clogged. Where the filter elements are used in a blood dialysis circuit, they each have a two-layer structure consisting of a mesh screen of a plastic material such as nylon and having mesh size of 200μ and a mesh screen of also a plastic material and having a mesh size of 40μ, and are installed such that the former mesh screen is on the side of the blood-entering space and the latter on the side of the blood-exit space. With this arrangement, even if microaggregates such as fibrin aggregates which have been attached to the filtering surfaces of a dialyzer are released and introduced into blood remaining in a blood dialysis circuit when the blood is returned into the patient's body by passing physiological saline solution or air into the circuit from the inlet side, they can be captured by the filter elements.

It is known that stored blood contains microaggregates having a size of about 2 to 200μ, and material and mesh size of the filter element can be suitably selected based on the desired filtering efficiency.

Referring again to FIG. 1, between the filter support 18 and blood inlet 16 is defined a space (distributing chamber) 28 communicating with the blood-entering spaces 30 and 31. A distributing member or piece 29 of a wedge-shaped sectional profile extends from the filter support 18 into the distributing chamber 28. Blood having been introduced through the inlet 16 into the distributing chamber 28 is distributed by the distributing piece 29 to the blood-entering spaces 30 and 31.

Also, a joining chamber 26 is defined between the filter support 18 and blood outlet 17, and blood streams having passed from the blood-entering spaces 30 and 31 through the filter elements 14 and 15 to the blood-exit spaces 24 and 25 and downwardly flowing therethrough join each other in the joining chamber 26 before leaving the filter device through the outlet 17.

The construction of the frame 11 and filter support 18 is most clearly shown in FIG. 2. As is shown, the frame 11 has a flaring portion 27b terminating in a substantially circular portion 27a. The filter support 18 includes a plate member 19 which is integral with the frame 11 and is made of the same material as the frame, for instance high impact polystyrene. The opposite sides 20 and 21 of the plate member 19 are each provided with a plurality of (eleven in the Figure) parallel and equally spaced straight ribs 22 extending parallel to the line connecting the inlet 16 and outlet 17 and raised by about 1 mm. By virtue of the ribs 22, the filter elements are not in contact with the plate member 29 over the entire corresponding surface thereof, and thus the effective blood-exit spaces 24 and 25 are formed (as shown in FIG. 1). The plate member 19 is also provided on each side with a circular raised peripheral edge portion 23 which is raised to the same height as the ribs 22, and an edge portion of each of the filter elements 14 and 15 is welded to each raised edge portion 23.

The joining chamber 26 is formed by cutting off a portion of the plate member 29 on the side of the outlet 17. The end of each of the ribs 22 on the side of the outlet 17 is spaced apart from the raised edge portion 23, so that flow of blood from the blood-exit spaces 24 and 25 into the joining chamber 26 is not blocked whatsoever.

The distributing chamber 28 as shown in FIG. 3, laterally flares and has a length dimension greater than one half the diameter of the filter elements 14 and 15, for instance a length of 50 mm in the case where the diameter of the filter elements is about 90 mm, so that blood can uniformly directed toward each of the blood-entering spaces 30 and 31 each defined between each of the filter elements 14 and 15 and each of the side plates 12 and 13.

The side plates 12 and 13 are each formed on the inner side inclusive of a portion thereof corresponding to the distributing chamber 28 with a recess 32 of a small depth (for instance, 1 mm), thus defining the blood-entering spaces 30 and 31. Also, the recessed portion 32 of the inner side of each side plate is provided with two parallel straight ribs 34 raised by about 1 mm and extending parallel to the line connecting the inlet 16 and outlet 17. The ribs 34 can hold the filter elements 14 and 15 such that the elements are not in contact with the respective side plates 14 and 15 over the entire corresponding inner surfaces thereof and thus ensure flow of blood through the spaces 30 and 31 without being interrupted by the filter elements 14 and 15.

The peripheral edge of the frame 11 is formed on each side with a stepped portion 36, and the side plates 12 and 13 are each provided on the inner side with a ridge 38, which is received in the stepped portion 36, as shown in FIG. 1. Before assembly, the height of the ridge 38 is greater than the depth of the stepped portion 36, and at the time of assembly the ridge 38 is fitted in the stepped portion 36 and secured thereto by thermal fusion caused by supersonic heating while being pressed.

The outer surface of the side plates 12 and 13 may be provided with characters for the purpose of providing irregularities or provided with slip prevention irregularities by means of an embossing treatment.

The operation of the above blood filter device will now be described.

In the case of using the blood filter device with a blood transfusion set, a bottle needle (not shown) for connection to a blood bottle is connected to the inlet 16 via a tube, and a dripping device (not shown) is connected to the outlet 17 via a tube. The dripping device is in turn connected to an intravascular needle via a tube.

In this case, before starting the blood transfusion, air within the blood filter has to be purged by causing blood to flow thereinto for securing a maximum effective filtering area of the blood filter.

To this end, after piercing the bottle needle into the blood bottle, the blood filter and dripping device are inverted so that the outlet 17 is at the top, and the blood filter and dripping device are held such that they are below the blood level. In this way, since the blood filter is below the blood level in the blood bottle, blood is caused to slowly flow into the blood filter for purging air. When blood is collected in about one half of the dripping device after the completion of air purging from the blood filter, a clamp provided on a tube connected to the end of the dripping device is closed to bring an end to the air purging operation.

Then, the blood filter is inverted again so that the inlet 16 is at the top. In this state, the blood entering the blood filter through the inlet 16 drops into the distributing chamber 28. This state can be observed from the outside through the transparent side plate 12 or 13. It will be appreciated that the distributing chamber 28 serves also as a dropping and air trapping chamber, and monitoring for trapped air and of the flow of blood can be obtained.

The blood dropping into the distributing chamber is divided by the distributing piece 29 into two streams flowing into the respective blood-entering spaces 30 and 31. The distributing piece 29 permits smooth flow of the blood flowing into the filtering blood spaces 30 and 31, thus preventing damage to blood components. Further, by providing for smooth flow, partial flow can be prevented.

The blood flowing into the blood-entering spaces 30 and 31 passes through the filter elements 14 and 15 from the entire surfaces defining the respective spaces 30 and 31 into the blood-exit spaces 24 and 25. As the blood passes through the filter elements 14 and 15, microaggregates contained in the blood are captured thereby.

The blood having passed through the filter elements 14 and 15 flows through the blood-exit spaces 24 and 25 along the ribs 22 toward the joining chamber 26 without partial flow being caused. Since the blood-exit spaces 24 and 25 are formed between the plate member 29 and the respective filter elements 14 and 15 by the ribs 22, blood can smoothly flow into the joining chamber 26 without giving rise to a dead space and leaves the blood filter through the outlet 17.

Figure 4:
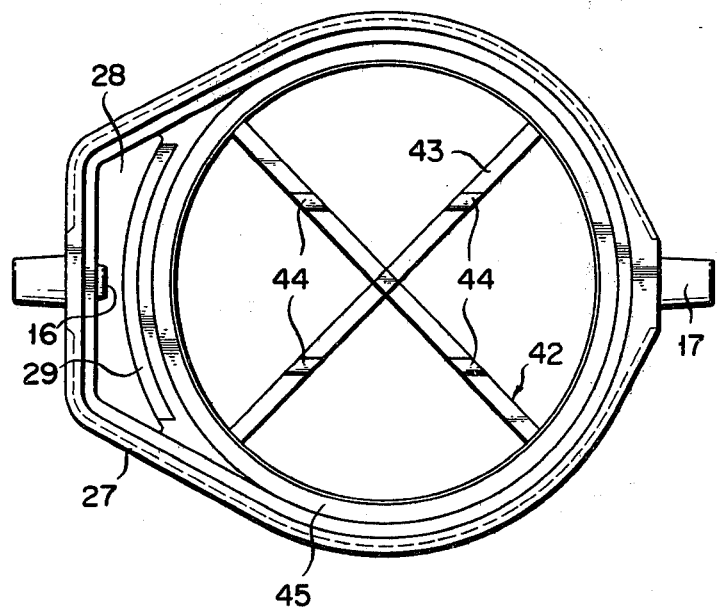
FIG. 4 is a plan view showing a frame and a filter support in another embodiment of the filter device according to the invention.

The above embodiment of the invention is by no means limitative, and various changes and modifications are possible. FIG. 4 shows a modification of the filter support. This example of the filter support can be used instead of the filter support 18 and comprises a pair of support rods 42 and 43 arranged in the form of a cross and supported by the frame 11 within the filtering space defined thereby. These support rods 42 and 43 have a plurality of projections or raised portions provided above and below the crossing point. The raised portions 44 serve to support the filter elements 14 and 15 such that the elements are not in contact with the support rods 42 and 43 over the entire corresponding surfaces thereof. This filter support also has an edge portion 45 of the same construction as in the previous embodiment.

The filter device according to the invention may, if necessary, be used by directly coupling a bottle needle and a dripping device respectively to the side of the inlet 16 and to the side of the outlet 17.

What we claim is:

1. A blood filter device comprising:
  a housing including a frame provided at opposite ends with an inlet and an outlet, said frame extending in a plane containing a line connecting said inlet and outlet; and a pair of side plates extending on opposite sides of said frame and defining a filtering space together with said frame;
  a filter support member disposed within said housing;
  a pair of substantially flat filter elements disposed on opposite sides of said filter support member such that each of said filter elements defines together with said filter support member a blood-exit space communicating with said outlet and defines together with the associated one of said side plates a blood-entering space communicating with said inlet;
  a distributing and air trapping chamber defined between said filter support and said inlet and communicating with each of said blood-entering spaces, said distributing and air trapping chamber, in use, being above said blood-entering spaces, and defining a space sufficient in size to receive blood from said inlet to trap air contained in the blood and present in the filter device to prevent such air from reaching said filter elements; and
  a distributing member extending from said filter support member into said distributing and air trapping chamber for substantially equally distributing blood having been introduced through said inlet into said distributing chamber to said blood-entering spaces.

2. A blood filter device according to claim 1, wherein said filter support includes a plate member integral with said frame and extending along a line connecting said inlet and outlet, said plate member dividing said filtering space into two sections, and a plurality of parallel ribs provided on each side of said plate member and extending parallel to the line connecting said inlet and outlet.

3. A blood filter device according to claim 2, wherein said filter support has a notch defining a joining chamber communicating with said outlet, blood streams flowing through said individual blood-leaving spaces joining each other in said joining chamber.

4. A blood filter device according to claim 1, wherein said filter support includes a pair of support rods in a cross-shaped arrangement and supported within said frame, and a plurality of raised portions provided on each side of said support rod.

5. A blood filter device according to any one of claims 1, 2, 3 or 4, wherein said substantially flat filter elements each have a lamination structure comprising a mesh screen and a plurality of non-woven fabric sheets, said mesh screen and non-woven fabric sheets being laminated in the mentioned order, and being mounted on said filter support such that said mesh screen is on the side of the corresponding blood-exit space.

6. A blood filter device according to claim 5, wherein said substantially flat filter elements each have a five-layer structure consisting of a mesh screen of nylon and having a mesh size of 170 to 200μ, a non-woven fabric sheet of nylon and having a thickness of about 200μ and a mesh size of about 35μ and three non-woven fabric sheets of nylon and having a thickness of about 350μ and a mesh size of about 25μ, said mesh screen and non-woven fabric sheets being laminated in the mentioned order, and being mounted such that said mesh screen is on the side of the corresponding blood-leaving space.

7. A blood filter device according to any one of claims 1, 2, 3 or 4, wherein said substantially flat filter elements each have a structure comprising of an upstream mesh screen of nylon and having a mesh size of 200μ and a downstream mesh screen of nylon having a mesh size of 40μ.

8. A blood filter device according to claim 1, wherein said blood-entering spaces are substantially vertically arranged and are adjacent each other, and wherein said distributing member extends above said blood-entering spaces substantially equidistant between said blood-entering spaces for substantially equally distributing blood introduced through said inlet to said blood-entering spaces.

* * * * *

UNITED STATES PATENT AND TRADEMARK OFFICE
CERTIFICATE OF CORRECTION

PATENT NO. : 4,304,670
DATED : December 8, 1981
INVENTOR(S) : Masaharu WATANABE et al It is certified that error appears in the above—identified patent and that said Letters Patent is hereby corrected as shown below:

COLUMN 1, line 14, change "microaggregates will, they cause" to --microaggregates, they will cause--.

Signed and Sealed this

Fourth Day of May 1982

[SEAL]

Attest:

GERALD J. MOSSINGHOFF

Attesting Officer

Commissioner of Patents and Trademarks